(12) United States Patent
Motai

(10) Patent No.: US 10,765,421 B2
(45) Date of Patent: Sep. 8, 2020

(54) PUSHING TOOL, TISSUE-SUTURING SYSTEM AND METHOD OF SUTURING A HOLLOW ORGAN

(71) Applicant: OLYMPUS CORPORATION, Hachioji-shi, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 200 days.

(21) Appl. No.: 15/860,521

(22) Filed: Jan. 2, 2018

(65) Prior Publication Data

US 2018/0125478 A1 May 10, 2018

Related U.S. Application Data

(63) Continuation of application No. PCT/JP2016/062379, filed on Apr. 19, 2016.

(30) Foreign Application Priority Data

Jul. 14, 2015 (JP) .................................. 2015-140441

(51) Int. Cl.
*A61B 17/04* (2006.01)
*A61B 17/02* (2006.01)
(Continued)

(52) U.S. Cl.
CPC ...... *A61B 17/0469* (2013.01); *A61B 17/0218* (2013.01); *A61B 17/0482* (2013.01);
(Continued)

(58) Field of Classification Search
CPC .......... A61B 2017/00818; A61B 2017/00331; A61B 2017/2927; A61B 2017/306;
(Continued)

(56) References Cited

U.S. PATENT DOCUMENTS 5,405,073 A 4/1995 Porter
6,656,113 B2 12/2003 Green, II et al.
(Continued)

FOREIGN PATENT DOCUMENTS

CN 202497179 U 10/2012
EP 3292824 A1 3/2018
(Continued)

OTHER PUBLICATIONS

Feb. 12, 2019 Extended European Search Report issued in European Patent Application No. 16824118.0.
(Continued)

*Primary Examiner* — Jocelin C Tanner
(74) *Attorney, Agent, or Firm* — Oliff PLC

(57) ABSTRACT

A pushing tool of the present invention includes a tissue pushing part having a shaft portion that is formed in a rod-shape, a linear portion including a pressing portion that is connected to the shaft portion and extends in a longitudinal direction, and a stopper maintaining an angle between the shaft portion and the linear portion at a desired angle when the pressing portion is closely pressed against an outer surface of a hollow organ.

3 Claims, 6 Drawing Sheets

(51) Int. Cl.
  *A61B 17/00* (2006.01)
  *A61B 17/29* (2006.01)
  *A61B 17/30* (2006.01)
  *A61B 90/00* (2016.01)

(52) U.S. Cl.
  CPC .................. *A61B 17/00491* (2013.01); *A61B 2017/00331* (2013.01); *A61B 2017/00818* (2013.01); *A61B 2017/2927* (2013.01); *A61B 2017/306* (2013.01); *A61B 2090/0817* (2016.02); *A61B 2217/005* (2013.01)

(58) Field of Classification Search
  CPC .......... A61B 17/0218; A61B 17/00491; A61B 17/0469; A61B 17/0482; A61B 2019/0817; A61B 2217/005
  See application file for complete search history.

(56) References Cited

U.S. PATENT DOCUMENTS

| | | |
|---|---|---|
| 8,057,490 B2 | 11/2011 | Harris et al. |
| 2004/0034371 A1* | 2/2004 | Lehman ............. A61B 17/0469 606/144 |
| 2008/0147112 A1 | 6/2008 | Sheets et al. |
| 2008/0249566 A1* | 10/2008 | Harris ................ A61B 17/0684 606/220 |
| 2009/0312602 A1 | 12/2009 | Sakamoto et al. |
| 2010/0087711 A1 | 4/2010 | Edwards |
| 2011/0066167 A1 | 3/2011 | Harris et al. |
| 2012/0165845 A1 | 6/2012 | Harris et al. |
| 2013/0072749 A1 | 3/2013 | Fairneny et al. |

FOREIGN PATENT DOCUMENTS

| | | |
|---|---|---|
| JP | 2003-235857 A | 8/2003 |
| JP | 2007-029195 A | 2/2007 |
| JP | 2008-110210 A | 5/2008 |
| WO | 2005/107605 A1 | 11/2005 |

OTHER PUBLICATIONS

May 30, 2017 Office Action issued in Japanese Patent Application No. 2017-512065.
Jul. 12, 2016 International Search Report issued in International Patent Application No. PCT/JP2016/062379.
Nov. 5, 2019 Office Action issued in Chinese Patent Application No. 201680040794.1.
May 11, 2020 Office Action issued in Chinese Patent Application No. 201680040794.1.

* cited by examiner

US 10,765,421 B2

PUSHING TOOL, TISSUE-SUTURING SYSTEM AND METHOD OF SUTURING A HOLLOW ORGAN

CROSS REFERENCE TO RELATED APPLICATIONS

This application is a continuation application based on a PCT Patent Application No. PCT/JP2016/062379, filed on Apr. 19, 2016, whose priority is claimed on Japanese Application No. 2015-140441, filed on Jul. 14, 2015, the entire content of which are hereby incorporated by reference.

BACKGROUND OF THE INVENTION

Field of the Invention

The present invention relates to a tissue-suturing system.

Description of the Related Art

Conventionally, an operative procedure called laparoscopic greater curvature plication (LGCP) is performed on patients with obesity. LGCP is an operative procedure of folding (hereinafter, this action is referred to as "inversion") a part of stomach to protrude to a lumen side along a greater curvature, and holding sites approximated by the inversion using sutures to prevent the sites from being separated from each other, and is performed laparoscopically. The part of the stomach is inverted, and thereby the substantial volume of the stomach becomes smaller compared to before the operative procedure is performed. Thus, the patients can more easily achieve a sense of fullness, and can reduce an amount of ingested food.

A medical instrument that can be used in inverting tissue is described in U.S. Pat. No. 8,057,490. This medical instrument includes a rod-shaped pressing member. When a stomach is pressed by a distal end of the pressing member, the pressed portion is inverted. A user sutures or locks approximated sites to prevent the sites from separating while holding the inverted state.

SUMMARY

A pushing tool of the present invention includes a tissue pushing part having a shaft portion that is formed in a rod-shape, a linear portion including a pressing portion that is connected to the shaft portion and extends in a longitudinal direction, and a stopper maintaining an angle between the shaft portion and the linear portion at a desired angle when the pressing portion is closely pressed against an outer surface of a hollow organ A length of the pressing portion may be longer than a maximum dimension of the shaft portion in a radial direction.

The tissue pushing part may be deformable such that the shaft portion and the linear portion line up on the same line.

A tissue-suturing system of the present invention includes the above pushing tool, a suturing device having an inserting portion that is inserted into a body cavity, a suturing portion that is provided at a distal portion of the inserting portion, and configured to be capable of suturing of the hollow organ. The pushing tool is inserted into the inserting portion with the linear portion set to a distal end side.

In the above configuration, the linear portion may be capable of being housed in the inserting portion by being deformed such that the shaft portion and the linear portion line up on the same line.

In the above configuration, the suturing device may be configured to be capable of suturing the hollow organ using a suture member, and positioned so that a suturing direction that is a direction in which the suture member moves and a direction in which the pressing portion extends in a state in which the pressing portion protrudes from the inserting portion are at right angle.

A method of suturing a hollow organ of the present invention includes pressing closely a pressing portion extending in a longitudinal direction against an outer surface of the hollow organ, reducing an internal pressure of the hollow organ to invert a first site with which the pressing portion are in contact while maintaining the state in which the pressing portion is closely pressed against the outer surface, and suturing a second site and a third site, which face each other across an inversion line formed by inverting the first site, such that a predetermined positional relation is maintained.

A suture member hooked on the second site and the third site may be used when suturing the second site and the third site. A suturing direction that is a direction in which the suture member extends between the second site and the third site may be at a right angle with a direction in which the inversion line extends.

DETAILED DESCRIPTION OF THE PREFERRED EMBODIMENTS

Figure 1:
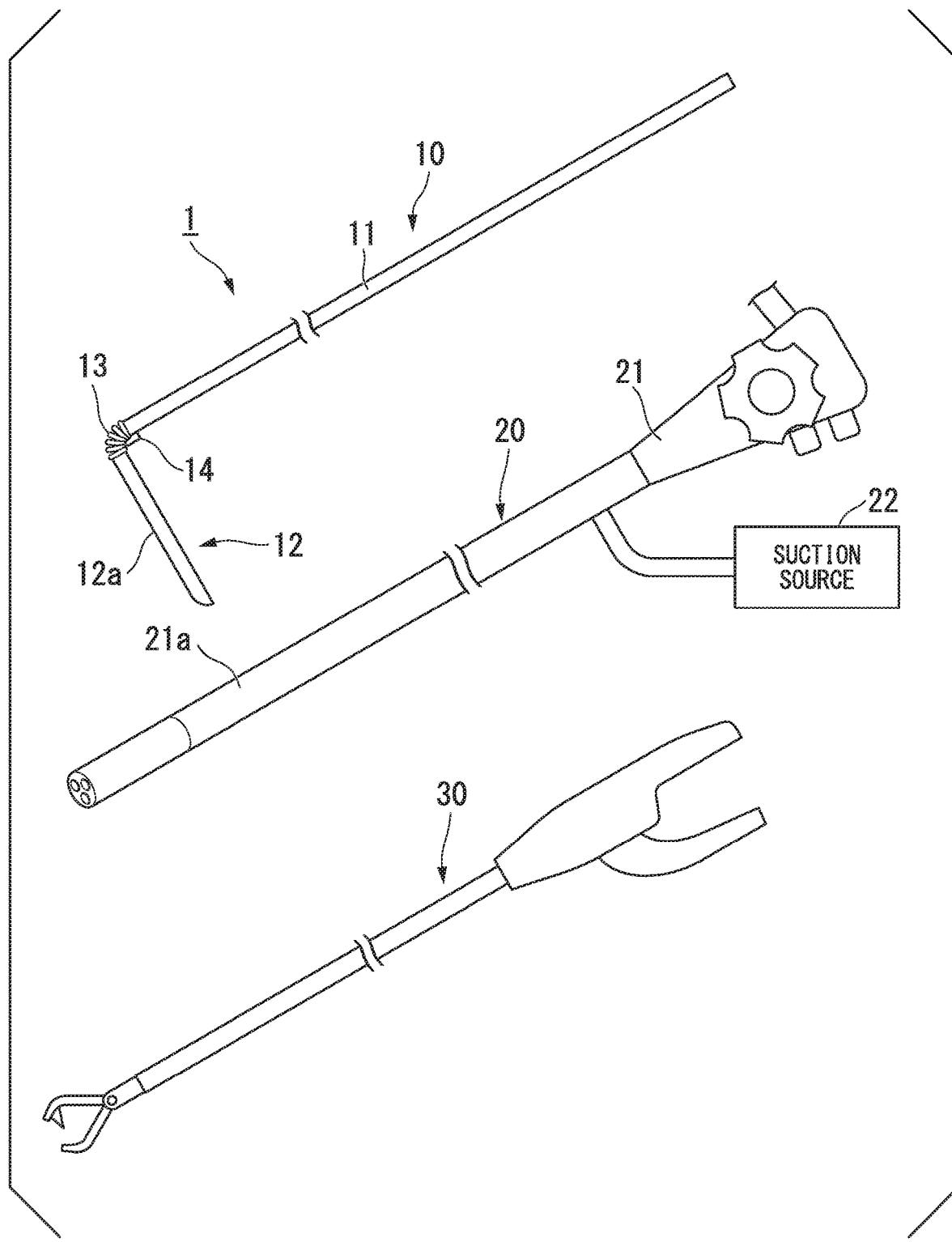
FIG. 1 is a view showing a tissue-suturing system according to a first embodiment of the present invention.

Hereinafter, a first embodiment of the present invention will be described with reference to FIGS. 1 to 6. FIG. 1 is a diagram showing a tissue-suturing system 1 of the present embodiment. A tissue-suturing system 1 includes a pushing tool (a tissue pushing part) 10 that inverts tissue, a suction device 20 configured to be capable of being introduced into a hollow organ, and a suturing device 30 configured to be capable of suturing the hollow organ.

The suction device 20 of the present embodiment includes a flexible endoscope 21 that be well-known in which an inserting portion 21a has flexibility, and a suction source 22 that is connected to a channel (not shown) provided in the inserting portion 21a of the flexible endoscope 21. The suction source 22 is driven, thereby enabling suction from the channel that is open to a distal end of the inserting portion 21a.

The suturing device 30 is a well-known device used in laparoscopic surgery, and is introduced into a body cavity via an access port of a trocar or the like retained in a body wall. An example of the suturing device 30 is shown in FIG. 1 in which a needle member to which a suture thread is attached is delivered between a pair of jaws and performs suturing. However, the suturing device is not limited thereto, and a variety of well-known suturing devices may be adequately selected and used.

The pushing tool 10 includes a shaft portion 11 that is long, and a linear portion 12 connected to a distal end of the shaft portion 11. The shaft portion 11 is formed in a rod shape by a metal or the like. The linear portion 12 is formed by a metal, a resin, or the like, and has a pressing portion 12a extending in a longitudinal direction. The shaft portion 11 has such rigidity as to maintain a linear state when the pressing portion 12a is closely pressed against an organ. A dimension of the linear portion 12 in the longitudinal direction (nearly equal to a length of the pressing portion 12a) is for instance about 50 millimeters, and is at least longer than a maximum dimension in a radial direction (a direction perpendicular to the longitudinal direction) of the shaft portion 11. The shape of the pressing portion 12a is not particularly restricted, and may be an elongate planar or curved shape, or a linear shape such as a ridge line.

The linear portion 12 is connected to the distal end of the shaft portion 11 via a joint portion 13 to be perpendicular to the shaft portion 11. The joint portion 13 is formed in a coil shape and is biased such that an angle formed between the linear portion 12 and the shaft portion 11 becomes an acute angle. The joint portion 13 supports the shaft portion 11 and the linear portion 12 such that the shaft portion 11 and the linear portion 12 become perpendicular by a stopper 14 described below in a natural state in which no external force is applied. When a force is applied in a direction opposite to a direction in which the joint portion 13 is biased, the joint portion 13 is capable of being deformed in a direction in which the angle formed by the shaft portion 11 and the linear portion 12 becomes an obtuse angle. Therefore, the pushing tool 10 is stretched in a linear shape or a nearly linear shape such that the shaft portion 11 and the linear portion 12 line up on the same line, and thereby can be easily inserted into the trocar or the like.

The stopper 14 coming into contact with the linear portion 12 is provided adjacent to the joint portion 13, and prevents the shaft portion 11 and the linear portion 12 from being at the acute angle by the deformation of the joint portion 13.

The angle between the shaft portion 11 and the linear portion 12 is a right angle in this natural state. Thus, when the pushing tool 10 is pushed to tissue, a force for pushing the shaft portion 11 can be applied by the linear portion 12 in a direction perpendicular to the tissue, and easily form inversion.

However, according to a positional relation between the access port and the target organ, an angle between the shaft portion 11 and a tissue surface with which the linear portion 12 comes into contact is not necessarily limited to a right angle. In this case, a position or an amount of protrusion of the stopper 14 may be preferably adjusted to come into contact with the tissue surface at a position at which the angle between the shaft portion 11 and the linear portion 12 becomes a desired angle (i.e., an acute angle or an obtuse angle) according to the angle between the shaft portion 11 and the tissue surface.

Movement of the tissue-suturing system 1 configured as described above when in use will be described with a case in which laparoscopic greater curvature plication (LGCP) is performed using the tissue-suturing system 1 given as an example. In the following description, an operator who manipulates the suction device 20 is referred to as a first operator, and an operator who manipulates the pushing tool 10 and the suturing device 30 is referred to as a second operator.

As preliminary work, the first operator introduces the suction device 20 into the stomach of a patient, and disposes the suction device 20 in a state in which a gas in the stomach can be suctioned. The second operator forms an access port for introducing observing means such as a laparoscope in the abdominal wall of the patient, and introduces the observing means to establish an environment in which the abdominal cavity can be observed. Further, an access port for introducing the pushing tool 10 and the suturing device 30 is formed in the abdominal wall. A method for forming the access port is not particularly restricted, and for example, may be performed by retaining a trocar in the abdominal wall. The access port may be prepared for each of the pushing tool 10 and the suturing device 30. Thereby, the preliminary work is finished.

The second operator inserts the pushing tool 10 into the access port in a nearly linear shape while observing the abdominal cavity using the observing means, and introduces the pushing tool 10 into the abdominal cavity. When the joint portion 13 of the pushing tool 10 comes out of the access port, the linear portion 12 returns to a state in which it is perpendicular to the shaft portion 11.

Subsequently, the second operator decides a position at which an inversion line will be formed, pushes the shaft portion 11, and presses portion 12a against the stomach so that the linear portion 12 runs along the inversion line.

The linear portion 12 is closely pressed against the stomach, and thereby a reaction force from the stomach acts on the linear portion 12. However, since the stopper 14 regulates movement of the linear portion 12, the shaft portion 11 and the linear portion 12 are held in a perpendicular state.

Figure 2:
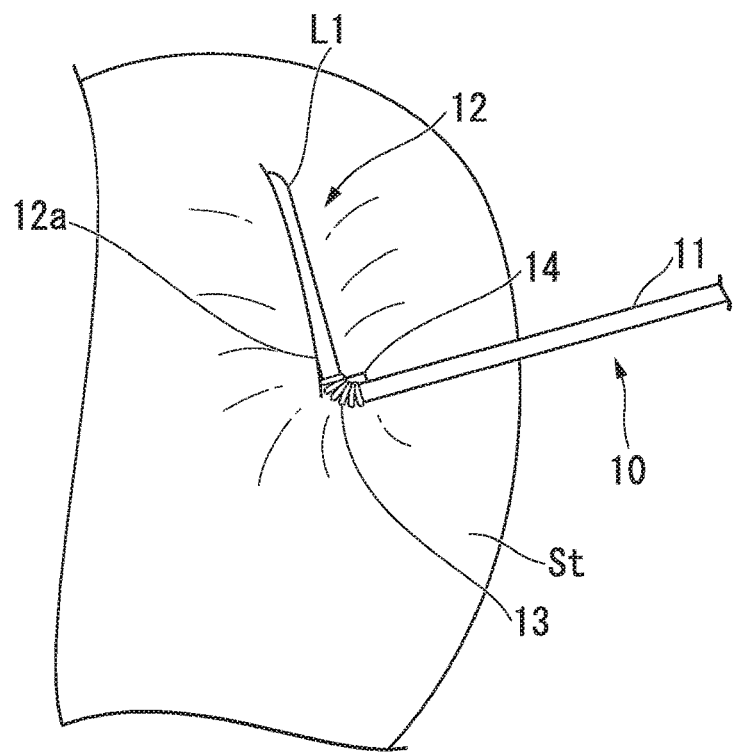
FIG. 2 is a view showing a process during use of the tissue-suturing system.

A site (a first site) of the stomach St against which the linear portion 12 is closely pressed is inverted toward the inside of the stomach St while forming the inversion line L1 along the linear portion 12 as shown in FIG. 2. However, when an internal pressure of the stomach St is in a high state, for example, because a large quantity of gas is present in the stomach St, tissue may not be sufficiently inverted.

Figure 3:
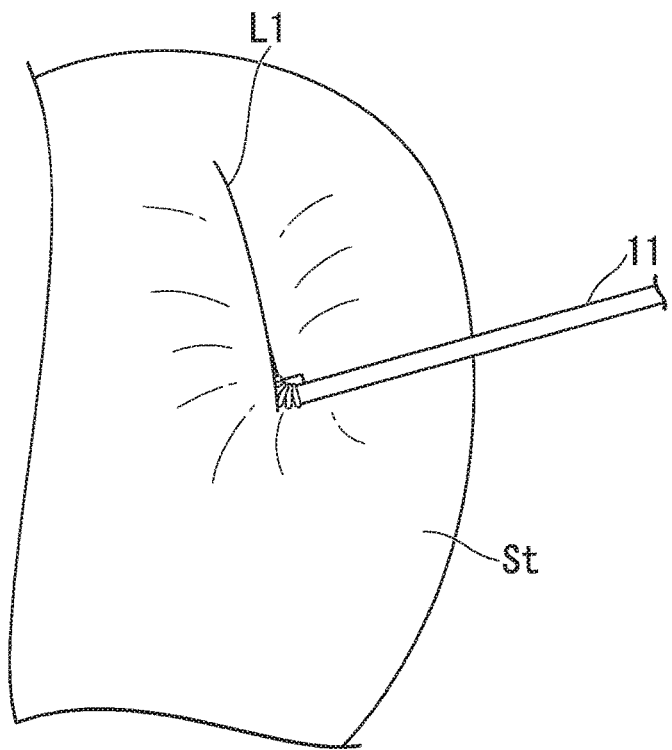
FIG. 3 is a view showing a process during use of the tissue-suturing system.

Accordingly, while the second operator continues to closely press the pushing tool 10 against the stomach St, the first operator drives the suction device 20 to suction the gas in the stomach St, and reduces the internal pressure of the stomach St (a second step). Due to the reduction of the internal pressure of the stomach St, the reaction force generated by the stomach St is weakened, and the first site pushed by the linear portion 12 is inverted more greatly. As a result, as shown in FIG. 3, the linear portion 12 is covered with the stomach St, and is not observed. The inversion line L1 is formed more deeply. Once the first site is inverted at a sufficient depth and a form of the inversion line L1 is suitable to perform a third step (to be described below), the first operator stops driving the suction device 20.

In the second step, the suction device 20 may be disposed not to be in contact with the inverted tissue. All gas in the hollow organ may be suctioned.

Figure 4:
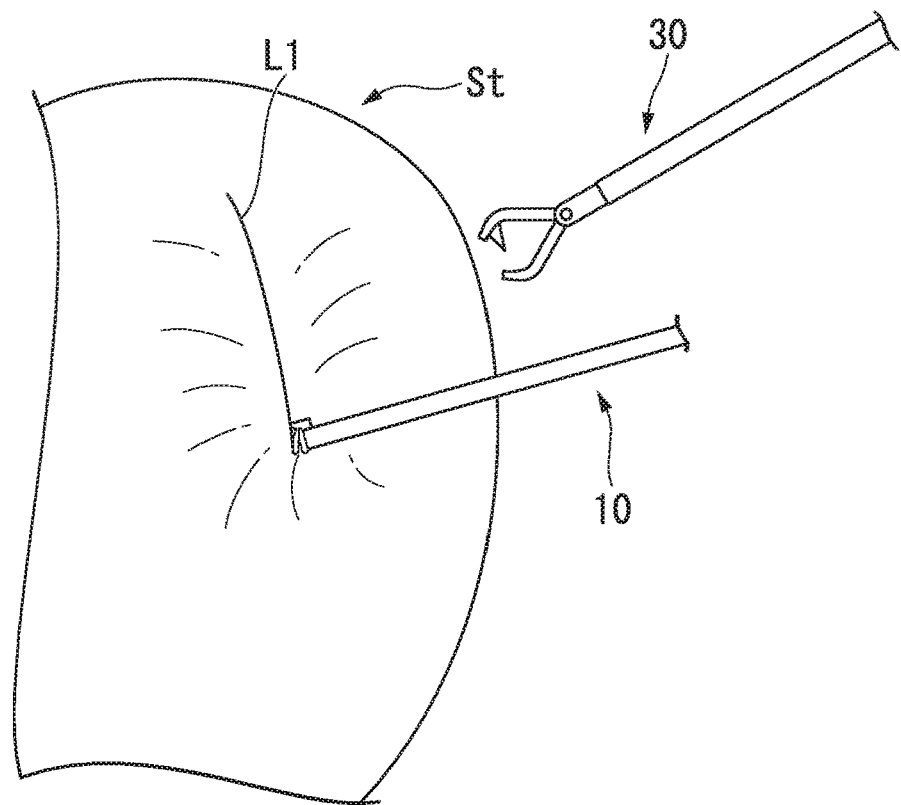
FIG. 4 is a view showing a process during use of the tissue-suturing system.
Figure 5:
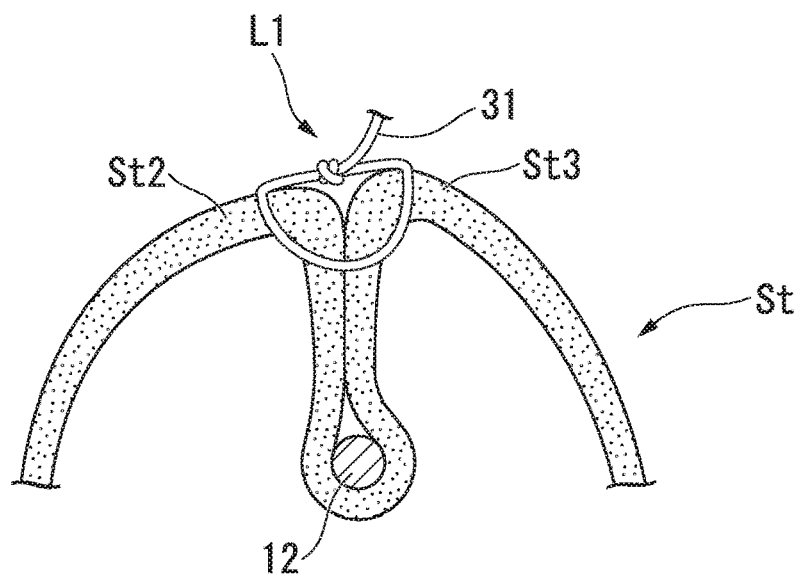
FIG. 5 is a view showing a process during use of the tissue-suturing system.

Next, the second operator introduces the suturing device 30 into the abdominal cavity and, as shown in FIG. 4, makes the suturing device 30 close to the formed inversion line L1. The second operator manipulates the suturing device 30 and, as shown in FIG. 5 in a sectional view, hooks a suture thread (a suture member) 31 on a site (a second site) St2 and a site (a third site) St3 of the stomach St which face each other across the inversion line L1, and sutures the second site St2 and the third site St3 to maintain a predetermined positional relation in which the second site St2 and the third site St3 get close to each other (a third step). An aspect of the suture is not particularly restricted, and may be adequately determined from a viewpoint of suitably maintaining the state in which the second site St2 and the third site St3 get close to each other. Therefore, as shown in FIG. 5, a plurality of annular sutures may be formed, or the suture may be performed by hooking a single suture thread on the tissue in a spiral shape. Further, the suture may be performed using a suture member other than the suture thread, such as, for instance, a clip.

When all the necessary sutures are completed, the second operator pulls out the pushing tool 10 to separate it from the stomach St. Since the state in which the second site St2 and the third site St3 get close to each other by the suture is maintained, even when the pushing tool 10 is separated from the stomach St, the inversion line L1 is still present between the second site St2 and the third site St3.

Up to now, one unit of the operational procedure of suturing the tissue while forming the inversion line L1 is completed. For example, when a length of the formed inversion line is not sufficient, the first to third steps are repeated again, and the inversion line has only to be extended up to a desired length.

Figure 6:
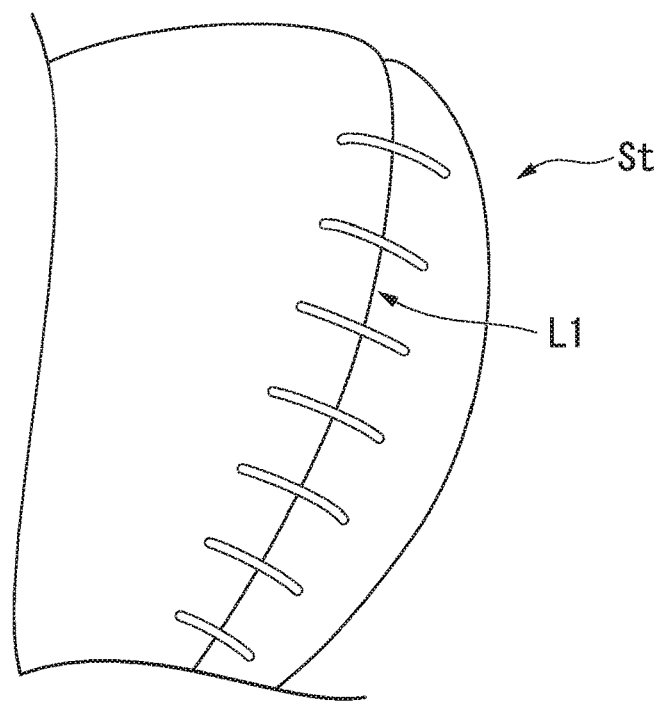
FIG. 6 is a view showing a stomach after LGCP.

A part of the stomach St for which LGCP is completed is shown in FIG. 6. A long inversion line L1 is formed along a greater curvature, and the suture is performed to cross the inversion line L1.

As described above, according to the tissue-suturing system 1 of the present embodiment, since the pushing tool 10 having the linear portion 12 is provided, a part of the hollow organ can be inverted by simple manipulation of closely pressing the pressing portion 12a against the target hollow organ so as to generate the inversion line L1 extending in one direction. Further, since the suction device 20 that is capable of being introduced into the hollow organ is provided, the inversion line L1 is enable to be formed in an aspect in which the suture is easily performed by the suturing device 30 by adequately adjusting the internal pressure of the hollow organ during the pushing motion caused by the pushing tool 10.

In the present embodiment, the operational procedure for applying the tissue-suturing system 1 with the LGCP given as an example has been described. However, the operational procedure for applying the tissue-suturing system of the present invention is not limited to the LGCP. For example, this procedure may also be applied to an operational procedure for excising a tumor of the digestive tract by cooperation of observing means or a treatment tool introduced from an access port into the abdominal cavity with an endoscope or a treatment tool introduced into the digestive tract. That is, the aforementioned first to third steps are performed to invert the tumor and surrounding tissue thereof, and the inverted state is maintained by suture. Then, the excision of the tumor from the inside of the hollow organ can be performed using a well-known stapler or the like.

Next, a second embodiment of the present invention will be described with reference to FIG. 7. In the present embodiment, an example in which the tissue pushing part and the suturing device are integrated will be described. In the following description, components common with those described previously will be given the same reference signs, and duplicate descriptions thereof will be omitted.

A tissue-suturing system of the present embodiment includes a suturing device 50 having a tissue pushing part 60 instead of the pushing tool 10 and the suturing device 30.

Figure 7:
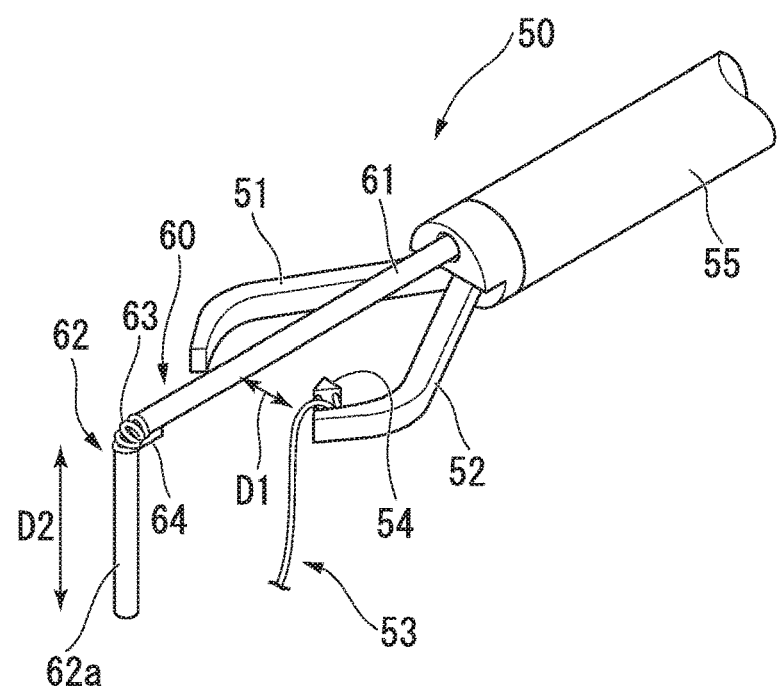
FIG. 7 is a view showing a distal portion of a suturing device in a tissue-suturing system according to a second embodiment of the present invention.

FIG. 7 is a view showing a distal portion of the suturing device 50. In the suturing device 50, a mechanism of the distal end for performing suture is roughly identical to the suturing device 30 of the first embodiment. That is, the mechanism has a well-known structure in which the suture is performed by delivering a needle portion 54 attached to a suture thread unit 53 between a pair of jaws (a suturing portion) 51 and 52 that are openable and closable and are provided at a distal portion of an inserting portion 55 inserted into the body cavity.

A structure of the tissue pushing part 60 is roughly identical to the pushing tool 10 in the first embodiment, and has a shaft portion 61, a linear portion 62, a joint portion 63, and a stopper 64. The shaft portion 61 is inserted into a channel (not shown) formed in the inserting portion 55 of the suturing device 50, and a proximal portion thereof is protruded by a manipulating portion (not shown). A user manipulates the proximal portion of the shaft portion 61, and thereby can advance and retract the tissue pushing part 60 with respect to the inserting portion 55.

Therefore, the shaft portion 61 is greatly retracted, and thereby the shaft portion 61 and the linear portion 62 can be accommodated in the inserting portion 55 in an approximately linear shape while deforming the joint portion 63.

In the suturing device 50, a suturing direction D1 that is a direction in which a suture thread (not shown) moves as the needle portion 54 is delivered between the pair of jaws 51 and 52 and a direction D2 in which a pressing portion 62a of the linear portion 62 protruding from a distal end of the inserting portion 55 extends in a natural state are at a right angle or an approximately right angle. The suturing direction D1 is a direction in which a suture member such as a suture thread for suturing a second site and a third site extends between the second site and the third site facing each other across an inversion line.

The tissue pushing part 60 is positioned to prevent rotation around an axis of the shaft portion 61 so as not to have a change of the direction D2 when advanced and retracted with respect to the inserting portion 55, and is inserted into the channel. This constitution can be realized, for instance, by providing a key at the shaft portion 61 and engaging the key with a key groove provided in the channel.

A motion of the tissue-suturing system of the present embodiment having the suturing device 50 configured as described above when in use will be described.

When the suturing device 50 is introduced into the abdominal cavity, the linear portion 62 of the tissue pushing part 60 in state that being accommodated in the inserting portion 55 is inserted into an access port. When the tissue pushing part 60 is advanced with respect to the inserting portion 55 after the suturing device 50 is introduced into the abdominal cavity, the linear portion 62 protrudes from the distal end of the inserting portion 55, and extends in the direction D2. In this state, the pressing portion 62a is closely pressed against an outer surface of the target hollow organ, the first step and the second step are performed as in the first embodiment. Subsequently, the second operator manipulates the manipulating portion to open and close the pair of jaws 51 and 52, and performs the third step.

Even in the tissue-suturing system of the present embodiment, as in the first embodiment, a part of the hollow organ can be inverted by simple manipulation of closely pressing the pressing portion so as to generate the inversion line extending in one direction. The inversion line can be formed in a suitable aspect by adjusting the internal pressure of the hollow organ.

Since the tissue pushing part 60 is integrated with the suturing device 50, the tissue pushing part 60 and the suturing device 50 are capable of being introduced from a single access port into a body cavity, and a burden of the patient is enable to be reduced. Further, the user is capable of performing both of the inversion and the suture of the tissue with one hand, and fluctuation caused by relative movement between the tissue pushing part 60 and the suturing device 50 in the third step is also hardly generated.

In addition, since the linear portion 62 is configured to be capable of being accommodated in the inserting portion 55, the linear portion 62 is capable of being easily inserted into the access port, and be easily introduced into the body cavity.

Since the suturing direction D1 and the extending direction D2 of the pressing portion 62a are positioned to be at the right angle or the approximately right angle, the suture perpendicular to the inversion line is enable to be stably performed. As a result, a situation of, for instance, relative movement between the second site and the third site facing each other across the inversion line after the suture can be suitably prevented.

Figure 8:
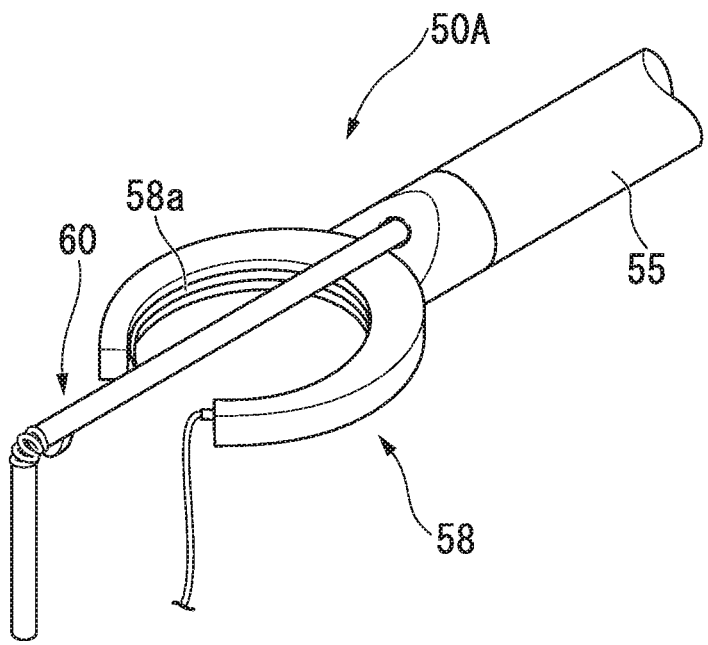
FIG. 8 is a view showing the distal portion of the suturing device in the tissue-suturing system according to the second embodiment of the present invention.

In the present embodiment, as an example of the suturing portion, the example in which the pair of jaws is provided has been described. However, a suturing device 50A of the present embodiment may be configured, for instance, by integrating the tissue pushing part 60 into a suturing device having a well-known suturing portion 58 for driving a curved needle 58a as shown in FIG. 8.

Although the embodiments of the present invention have been described, the technical scope of the present invention is not limited to the above embodiments, and is enable to change combinations of the components, or variously modify or eliminate each component without departing from the spirit and scope of the present invention.

For example, in the tissue-suturing system of the present invention, the constitution of the tissue pushing part is not limited to the aforementioned constitution. A modification of the tissue pushing part is shown below.

Figure 9:
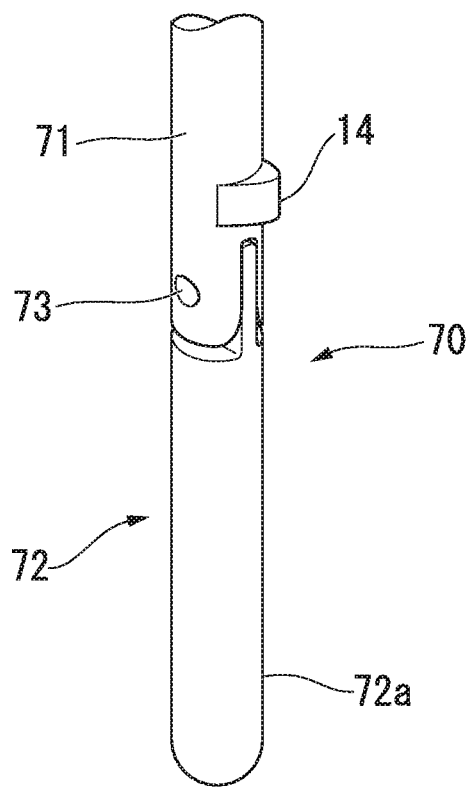
FIG. 9 is a view showing a distal portion of a tissue pushing part of a modification of the present invention.

In a tissue pushing part 70 of a modification shown in FIG. 9, a shaft portion 71 and a linear portion 72 having a pressing portion 72a are coupled by a rotation shaft 73 to be relatively rotated. Since the shaft portion 71 and the linear portion 72 are smoothly relatively rotated without nearly generating resistance, when the shaft portion 71 is held to extend in a vertical direction with the linear portion 72 located at a lower side, the linear portion 72 rotates under its own weight, and the shaft portion 71 and the linear portion 72 become linear. For this reason, introduction into a body cavity via an access port is easy. When tissue is inverted, the pressing portion 72a has only to be closely pressed against the tissue with the linear portion 72 rotated to a side of the stopper 14.

Figure 10:
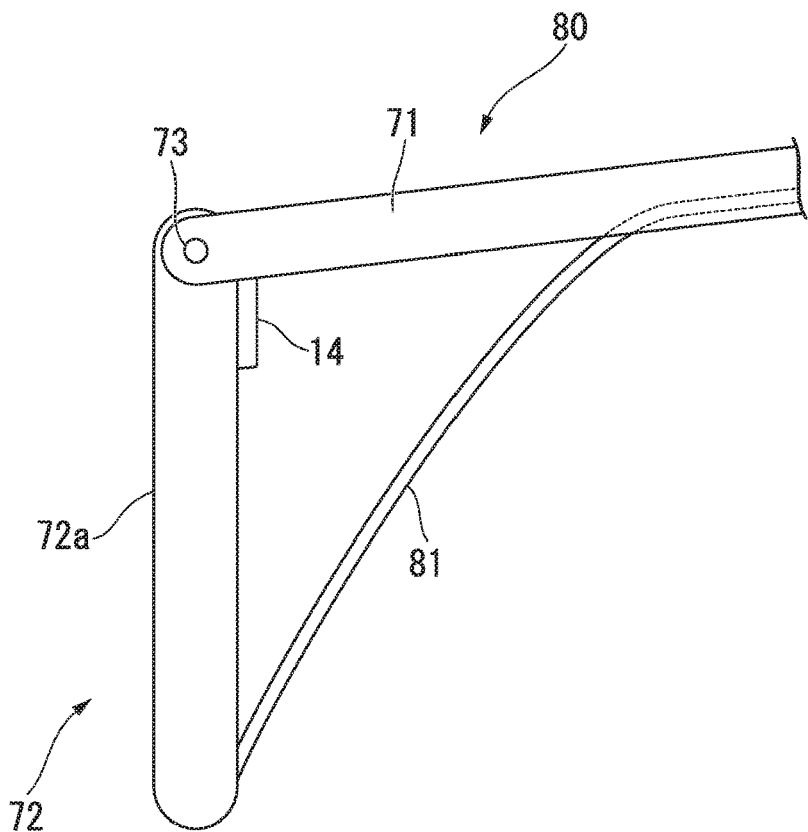
FIG. 10 is a view showing a distal portion of a tissue pushing part of a modification of the present invention.

In a tissue pushing part 80 of a modification shown in FIG. 10, a manipulating wire 81 connected to a distal end of a linear portion 72 of the tissue pushing part 70. Since the manipulating wire 81 protrudes from a proximal portion of a shaft portion 71 through the inside of the shaft portion 71, the manipulating wire 81 is pulled to the proximal end side, and thereby the shaft portion 71 and the linear portion 72 can be changed into a perpendicular state at an arbitrary timing even when the pressing portion 72a is not closely pressed against the tissue.

The constitution of the above modification may also be applied to a case in which there is no integration with the suturing device like the pushing tool 10.

The suturing device in the tissue-suturing system of the present invention is not limited to suturing the tissue using the suture member. For example, a treatment tool in which high frequency energy, resistance heating energy, laser energy, a biological adhesive, or the like is applied to the tissue and thereby the second site and the third site is capable of being joined to maintain a predetermined position relation is also included in the suturing device in the present invention.

Figure 11:
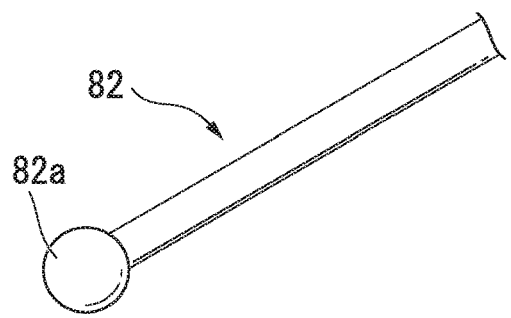
FIG. 11 is a view showing a distal portion of a tissue pushing part of a modification of the present invention.
Figure 12:
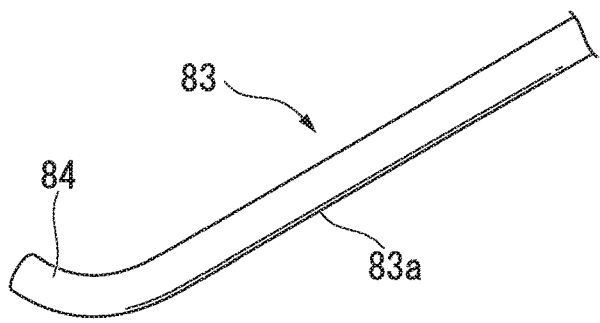
FIG. 12 is a view showing a distal portion of a tissue pushing part of a modification of the present invention.

In the tissue pushing part, the shape of the linear portion may be modified. For example, like a linear portion 82 of a modification shown in FIG. 11, a distal end face may be formed in a spherical shape by forming only a distal portion 82a in a large diameter, or like a linear portion 83 of a modification shown in FIG. 12, a distal portion 84 may be slightly bent in a direction away from a pressing portion 83a. In this way, when the linear portion is closely pressed against the tissue in order to invert the tissue, a pointed portion does not come into contact with the tissue, and thus a burden on the tissue is enable to be reduced.

Further, the hollow organ to which the tissue-suturing system of the present invention can be applied is not limited to the aforementioned stomach. Therefore, the tissue-suturing system may also be applied to the esophagus, the duodenum, the colon, or the like.

The invention claimed is:

1. A method of suturing a hollow organ comprising:
   manipulating a pushing tool having a shaft portion and a linear portion including a pressing portion, so as to form an angle between the shaft portion and the linear portion;
   pressing closely the pressing portion extending in a longitudinal direction against an outer surface of the hollow organ;
   reducing an internal pressure of the hollow organ to invert a first site with which the pressing portion is in contact while maintaining a state in which the pressing portion is closely pressed against the outer surface; and
   suturing a second site and a third site, which face each other across an inversion line formed by inverting the first site, such that a predetermined positional relation is maintained,
   wherein the angle formed between the shaft portion and the linear portion is a right angle.

2. The method of suturing a hollow organ according to claim 1, wherein the pressing portion is provided on a side of the linear portion.

3. The method of suturing a hollow organ according to claim 1, wherein:
   a suture member hooked on the second site and the third site is used when suturing the second site and the third site; and
   a suturing direction that is a direction in which the suture member extends between the second site and the third site is at a right angle with a direction in which the inversion line extends.

* * * * *